(12) United States Patent
Xie et al.

(10) Patent No.: US 12,394,247 B2
(45) Date of Patent: Aug. 19, 2025

(54) ADVANCED MENTAL FATIGUE EARLY WARNING SYSTEM, ELECTRONIC DEVICE AND STORAGE MEDIUM

(71) Applicant: Air Force Medical University, Shaanxi (CN)

(72) Inventors: Kangning Xie, Shaanxi (CN); Yan Li, Shaanxi (CN); Chi Tang, Shaanxi (CN); Erping Luo, Shaanxi (CN); Yawen Zhai, Shaanxi (CN); Jiaojiao Ma, Shaanxi (CN); Juan Liu, Shaanxi (CN); Da Jing, Shaanxi (CN); Zedong Yan, Shaanxi (CN)

( * ) Notice: Subject to any disclaimer, the term of this patent is extended or adjusted under 35 U.S.C. 154(b) by 171 days.

(21) Appl. No.: 18/500,233

(22) Filed: Nov. 2, 2023

(65) Prior Publication Data

US 2024/0144723 A1   May 2, 2024

(30) Foreign Application Priority Data

Jul. 25, 2023   (CN) .......................... 202310914092.3

(51) Int. Cl.
  *G06V 40/18*   (2022.01)
  *B60W 40/08*   (2012.01)
     (Continued)

(52) U.S. Cl.
  CPC ........... *G06V 40/193* (2022.01); *B60W 40/08* (2013.01); *B60W 50/16* (2013.01); *G06V 20/597* (2022.01);
     (Continued)

(58) Field of Classification Search
  CPC ... G06V 40/193; G06V 20/597; B60W 40/08; B60W 50/16; B60W 2050/143; B60W 2050/146
     (Continued)

(56) References Cited

U.S. PATENT DOCUMENTS 9,198,575 B1 * 12/2015 Blacutt ................ G06V 20/597
2004/0170304 A1 *  9/2004 Haven .................... G06V 40/19
                                                                382/115

(Continued)

*Primary Examiner* — Naomi J Small
(74) *Attorney, Agent, or Firm* — Addison D. Ault; IPGentleman Intellectual Property Services, LLC (57) ABSTRACT

The present disclosure discloses an advanced mental fatigue early warning system, electronic device and storage medium, including a data acquisition module, a preprocessing module, an adjustment ability calculation module, a fatigue early warning module, a communication module and a storage module; the data acquisition module is configured for obtaining pupil diameter data; the preprocessing module is configured for preprocessing the pupil diameter data, removing invalid data, and performing linear interpolation; the adjustment ability calculation module is configured for performing calculation and correcting the preprocessed pupil diameter data; the fatigue early warning module is configured for performing mathematical modeling, establishing an advanced prediction model, and calculating a remaining time for an upcoming mental fatigue occurs and issuing an alarm; the communication module is configured for uploading mental fatigue adjustment abilities and alarm methods; the storage module is configured for archiving intermediate data.

9 Claims, 4 Drawing Sheets

(51) Int. Cl.
   *B60W 50/16* (2020.01)
   *G06V 20/59* (2022.01)
   *B60W 50/14* (2020.01)

(52) U.S. Cl.
   CPC . *B60W 2050/143* (2013.01); *B60W 2050/146* (2013.01)

(58) Field of Classification Search
   USPC ...................................................... 340/425.5
   See application file for complete search history.

(56) References Cited

U.S. PATENT DOCUMENTS

| | | | |
|---|---|---|---|
| 2004/0233061 A1* | 11/2004 | Johns ..................... | G06V 40/19 340/575 |
| 2006/0203197 A1* | 9/2006 | Marshall ................ | A61B 5/163 351/246 |
| 2012/0069301 A1* | 3/2012 | Hirata ................... | A61B 5/4809 351/209 |
| 2017/0106873 A1* | 4/2017 | Fung ....................... | G01S 19/13 |
| 2018/0012090 A1* | 1/2018 | Herbst .................... | G06V 40/20 |
| 2019/0077409 A1* | 3/2019 | Zandi ...................... | G06F 3/013 |
| 2019/0370582 A1* | 12/2019 | Schmidt ............... | G06V 20/597 |
| 2020/0151474 A1* | 5/2020 | Zandi ...................... | G06F 3/013 |
| 2022/0292880 A1* | 9/2022 | Oguni ...................... | G06T 7/73 |

\* cited by examiner

ADVANCED MENTAL FATIGUE EARLY WARNING SYSTEM, ELECTRONIC DEVICE AND STORAGE MEDIUM

CROSS-REFERENCE TO RELATED APPLICATION

This application claims priority to Chinese Patent Application No. 202310914092.3, filed on Jul. 25, 2023 before the China National Intellectual Property Administration, the disclosure of which is incorporated herein by reference in entirety.

TECHNICAL FIELD

The present disclosure relates to the field of neuroscience and signal processing, and in particular to an advanced mental fatigue early warning system, an electronic device and a computer-readable storage medium.

BACKGROUND

The fatigue of vehicle drivers, pilots, controllers, etc. is mainly manifested as mental fatigue (sometimes called cognitive fatigue). The characteristics of mental fatigue are the cover-up effect in the early stage and the sudden effect in the later stage. In layman's terms, although it does not seem tired in the initial stage of the work, mental fatigue keeps accumulating, and the mind wanders and doze happen unknowingly in the middle and later stages. The cover-up effect in the early stage and the suddenness in the middle and later stages have brought about major hidden dangers with short warning time. Explicit mental fatigue is a result of joint action of two internal factors, one is the gradually accumulated physiological mental fatigue, which reflects the continuous consumption of cognitive resources, the other is the regulatory system, which reflects the regulatory and compensatory effects of high-level cognition, it can cover up the physiological fatigue in the early stage, usually after 30-120 minutes of work, the physiological fatigue cannot be covered up, then mental fatigue will appear. Conventional indicators include facial expression, percentage of eyelid closure, and electroencephalogram, etc. Such indicators belong to the range of "post-fatigue measurement", and manifest serious potential safety hazard.

For example, the Chinese patent application with application number CN200920160060.4 provides a held-in-mouth fatigue early warning device. Under normal circumstances, the teeth are clenched and the alarm is not triggered. When fatigue or lack of concentration, the alarm is released and the buzzer starts the warning. This method requires the alarm to be bitten at all times, causing interference to the driver, and when fatigue is detected, the fatigue has reached a very dangerous level, so the prompting effect on safe driving needs to be improved. In the Chinese patent application of "Prediction System for Fatigue State of Car Driver" with application number CN201310229235.3, it uses the driver's eye closing time as a parameter to activate the alarm. It can be seen that all the above methods belong to "post-fatigue measurement". When fatigue is measured, mental fatigue has already appeared, that means the fatigue has reached a very dangerous level. Therefore it poses serious safety risks and the prompting effect on safe driving needs to be improved.

To sum up, most of the current mental fatigue measurement methods reflect the external manifestations of mental fatigue from different aspects and reflect the regulation results of physiological mental fatigue by the regulatory system (physiological fatigue is covered up). Therefore, it can only be measured after the physiological mental fatigue has accumulated to a large enough level (the cover-up effect fails) and the mental fatigue is manifested. Early warning systems based on this post-fatigue measurement method often have the problem of warning lag and cannot intelligently warn the driver in advance.

SUMMARY

In view of the above existing problems, the present disclosure aims to provide a mental fatigue early warning system that: (1) overcomes the cover-up effect of mental fatigue: the mental fatigue detection is changed from the traditional "post-fatigue measurement" to "pre-fatigue measurement" based on the advanced prediction model; (2) that is used to carry out intelligent prediction and intervention of mental fatigue.

In order to achieve the above objects, the technical solutions adopted by the present disclosure are as follows:

An advanced mental fatigue early warning system, comprising a data acquisition module, a preprocessing module, an adjustment ability calculation module, a fatigue early warning module, a communication module and a storage module;

the data acquisition module is configured for obtaining pupil diameter data of an operator to be monitored;

the preprocessing module is configured for preprocessing the pupil diameter data, removing invalid data, and performing linear interpolation to obtain preprocessed pupil diameter data;

the adjustment ability calculation module is configured for performing calculation based on the preprocessed pupil diameter data and correcting the preprocessed pupil diameter data through an ambient light index to obtain a constantly updated adjustment ability time series;

the fatigue early warning module is configured for performing mathematical modeling based on the obtained adjustment ability time series, establishing an advanced prediction model, and calculating a remaining time for an upcoming mental fatigue occurs and issuing an alarm;

the communication module is configured for uploading mental fatigue adjustment abilities and alarm methods to a remote server to facilitate management monitoring;

the storage module is configured for archiving intermediate data.

According to some embodiments of the present disclosure, the fatigue early warning module comprises a mental fatigue occurrence time prediction sub-module and an alarm intensity setting sub-module;

the mental fatigue occurrence time prediction sub-module is configured for establishing the advanced prediction model based on the obtained adjustment ability time series, and obtaining a prediction line which has not yet occurred by means of the advanced prediction model, and then intersecting the obtained prediction line with a predetermined threshold line to calculate the remaining time for the upcoming mental fatigue;

the alarm intensity setting sub-module is configured for comparing the obtained remaining time for the upcoming mental fatigue with a threshold set by a user, triggering different alarm intensities, and issuing alarms according to different alarm intensities.

According to some embodiments of the present disclosure, the alarm intensities are divided into several levels, and different levels of alarm intensity correspond to different alarm sounds, voices and vibration intensities.

According to some embodiments of the present disclosure, a method for constructing the advanced prediction model comprises:

step 1: obtaining the pupil diameter data of a current person to be monitored and ambient light data, preprocessing the pupil diameter data, removing abnormal values, and performing a linear interpolation for the vacancies after removing the abnormal values, to obtain the preprocessed pupil diameter data;

step 2: defining an adjustment ability index based on the preprocessed pupil diameter data, and calculating the adjustment ability index to obtain adjustment ability index time series;

step 3: calculate the ambient light index based on the ambient light data, using an adaptive filter to remove ambient light interference, and obtaining corrected adjustment ability index time series;

step 4: constructing a mental fatigue adjustment ability prediction model based on the corrected adjustment ability index time series.

According to some embodiments of the present disclosure, the step 2 comprises:

step 21: recording pupil diameter time series as $x^{(1)}(i)$, $1 \leq i \leq N$, where N is a length of the time series, and taking a number m of points to form a vector $u_m(j)$.

$$u_m(j)=[x^{(1)}(j+k):0 \leq k \leq m-1];$$

step 22: defining a distance between vectors $u_m(i)$ and $u_m(j)$ as d:

$$d = \max_{k=0,1,\cdots,m-1} |x^{(1)}(i+k) - x^{(1)}(j+k)|;$$

step 23: calculating a standard deviation of the time series $x^{(1)}(i)$ as r, counting the number of all sets of vectors $u_m(i)$ and $u_m(j)$ that satisfy d<r, and recording it as $A_m$;

step 24: calculating $S^{(1)}$:

$$S^{(1)} = -\ln\left[\frac{A_{m+1}/(N-m-1)}{A_m/(N-m)}\right] \quad \text{(Formula 1)}$$

step 25: averaging every 2 values of the pupil diameter time series $x^{(1)}(i)$ as a new value to form a new time series $x^{(2)}(i)$, and repeating the steps 21-24 to get $S^{(2)}$;

step 26: repeating the step 25 to obtain $S^{(3)}$, $S^{(4)}$, ..., $S^{(\tau)}$ in sequence, where τ is a number in an interval [10, 30];

step 27: defining a calculation formula of the adjustment ability index as:

$$S = \frac{\sum_{i=1}^{\tau} S^{(i)}}{\tau}; \quad \text{(Formula 2)}$$

step 28: using a sliding window to calculate S, and a setting formula for a sliding window width is:

$$W = \frac{250\tau}{F_S} \quad \text{(Formula 3)}$$

where $F_S$ is a sampling frequency of pupil diameter;

step 29: obtaining the adjustment ability index time series S(n) according to the calculated adjustment ability index.

According to some embodiments of the present disclosure, the step 3 comprises:

step 31: collecting ambient light time series y(i), $1 \leq i \leq N$ through an environmental sensor, where N is a length of the time series, and taking a number m of points to form a vector $u_m(j)$:

$$u_m(j)=[y(j+k):0 \leq k \leq m-1];$$

step 32: defining a distance between vectors $u_m(i)$ and $u_m(j)$ as d:

$$d = \max_{k=0,1,\cdots,m-1} |y(i+k) - y(j+k)|;$$

step 33: calculating a standard deviation of the time series y(i) as r, counting the number of all sets of vectors $u_m(i)$ and $u_m(j)$ that satisfy d<r, and recording it as $A_m$;

step 34: obtaining T according to the Formula 1;

step 35: using a sliding window to calculate T and obtaining ambient light index time series $T_1$, $T_2$, $T_3$, ...;

step 36: redefining sliding window series of the adjustment ability index S(n) obtained in the step 29 as d(n), n=1, 2, ...;

step 37: representing d(n) as:

$$d(n)=S(n)+T_1(n), n=1,2,\cdots$$

where $T_1(n)$ is a pupil adjustment index component caused by the ambient light, S(n) is a real adjustment ability index component caused by a pupil;

$$e(n)=d(n)-z(n), n=1,2,\cdots$$

where e(n) is an error between d(n) and an adaptive filter output z(n);

step 38: calculating a weight vector w of the adaptive filter through an iterative method:

$$w(n+1)=w(n)+\mu[p-Rw(n)]$$

where n represents the number of iterations, μ represents a positive constant, p is a cross-correlation vector of the data, and R is a correlation matrix of the data;

step 39: obtaining the corrected adjustment ability index time series based on the obtained e(n).

According to some embodiments of the present disclosure, the constructed prediction model comprises a mental fatigue advanced prediction model configured to work in case where a manifestation occurrence time of mental fatigue is greater than 5 minutes from the current time and a mental fatigue precise prediction model configured to work in case where the manifestation occurrence time of mental fatigue is less than or equal to 5 minutes from the current time, approaching threshold:

(1) the mental fatigue advanced prediction model is constructed in the following steps:

step 41: define a loss function of the adjustment ability index time series:

$$\ell(\hat{S}-S)=(\hat{S}-S)^2 \quad \text{(Formula 4)};$$

step 42: for each input time point $t_n$, a predicted estimated value is:

$$\hat{S}_n=pt_n+b \quad \text{(Formula 5)}$$

step 43: defining an average loss function as:

$$L(p, b) = \frac{1}{N2}\sum_{n=1}^{N2} (\hat{S}_n - S_n)^2 = \frac{1}{N2}\sum_{n=1}^{N2} (pt_n + b - S_n)^2; \quad \text{(Formula 6)}$$

step 44: solving parameters which minimize L(p, b) according to Formula 7:

$$p^*, b^* = \arg\min_{p,b} L(p, b) = \arg\min_{p,b} \sum_{n=1}^{N2} (pt_n + b - S_n)^2; \quad \text{(Formula 7)}$$

and:

$$p^* = \frac{\frac{1}{N2}\sum_{n=1}^{N2} t_n S_n - \left(\frac{1}{N2}\sum_{n=1}^{N2} t_n\right)\left(\frac{1}{N2}\sum_{n=1}^{N2} S_n\right)}{\frac{1}{N2}\sum_{n=1}^{N2} t_n^2 - \left(\frac{1}{N2}\sum_{n=1}^{N2} t_n\right)^2} \quad \text{(Formula 8)}$$

$$b^* = \bar{S} - \bar{t} p^*. \quad \text{(Formula 9)}$$

(2) the mental fatigue precise prediction model is constructed in the following steps:

step 45: recording for a period of time during a real-time recording process;

step 46: after obtaining time-adjustment ability index time series $(t_1,S_1)$, $(t_2,S_2)$, • • • $(t_{N2},S_{N2})$ according to the above steps, establishing an autoregressive model, step 47: an order of the autoregressive model is selected as 50, a data window is 100 s, and it is updated every is to predict a waveform of 25 s.

An electronic device, comprising:

at least one processor; and a memory communicatively connected to the at least one processor;

wherein the memory is configured to store instructions executable by the at least one processor, the instructions are executed by the at least one processor, so that the at least one processor executes the steps in any one of the above embodiments.

A computer-readable storage medium storing computer instructions, wherein the computer instructions are used to allow a computer to execute the steps in any one of the above embodiments.

The beneficial effects of the present disclosure include:

First, the system proposed by the present disclosure can be directly installed on a vehicle carrier or workbench (such as a vehicle, an airplane, a ship, a drone operation station, an air traffic controller's workbench, etc.), it adopts a non-contact and interference-free collection equipment to collect pupil diameter, it does not require electrode contact or wearing. In addition, this system also sets multiple levels of alarm intensity. According to the intensity set by the user in advance, the corresponding alarm intensity may be used to alarm when fatigue is detected.

Second, the present disclosure proposes an advanced prediction model to predict mental fatigue through the adjustment ability index of pupil diameter, directly measures the cognitive adjustment ability, overcomes the limitations of traditional fatigue detection and prediction, and it is not subject to cover-up effects and sudden effects. Based on this prediction model, a mental fatigue early warning system is constructed. Through this early warning system, drivers of vehicles, aircrafts, etc. or instrument operators can be warned by voice, vibration, etc., to get corresponding alarms, before they reach the dangerous mental fatigue threshold, therefore it achieves pre-fatigue intervention.

DETAILED DESCRIPTION OF EMBODIMENTS

In order to enable those of ordinary skill in the art to better understand the technical solutions of the present disclosure, the technical solutions of the present disclosure will be further described below in conjunction with the accompanying drawings and embodiments.

Figure 1:
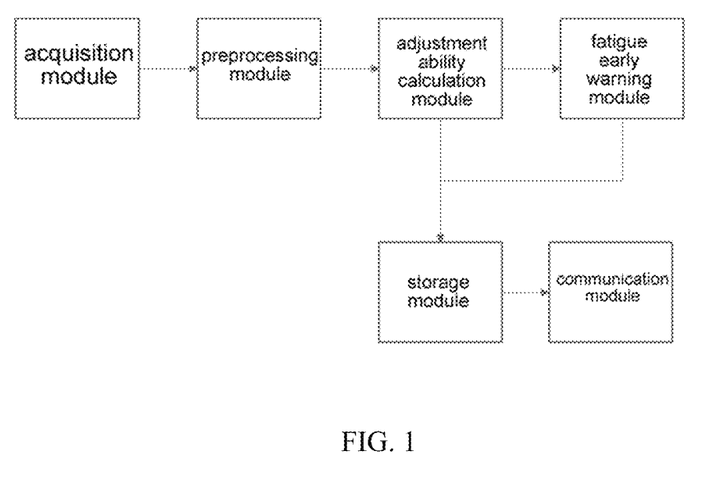
FIG. 1 is a module architecture diagram of this system.

As shown in FIG. 1, the present disclosure proposes a mental fatigue early warning system, which includes a data acquisition module, a preprocessing module, an adjustment ability calculation module, a fatigue early warning module, a storage module and a communication module.

The data acquisition module is configured for obtaining pupil diameter data of the person to be monitored (vehicle driver, pilot, drone driver, air traffic controller, etc.).

The preprocessing module is configured for preprocessing the pupil diameter data, removing invalid data, and performing linear interpolation to obtain preprocessed pupil diameter data.

The adjustment ability calculation module is configured for performing calculation based on the preprocessed pupil diameter data and correcting the preprocessed pupil diameter data through an ambient light index to obtain a constantly updated adjustment ability time series.

The fatigue early warning module includes a mental fatigue occurrence time prediction sub-module and an alarm intensity setting sub-module.

The mental fatigue occurrence time prediction sub-module is configured for performing mathematical modeling and establishing the advanced prediction model based on the obtained adjustment ability time series, and obtaining prediction complexity time series that has not yet occurred by means of the advanced prediction model, and then intersecting the obtained prediction line with a predetermined threshold line to calculate the remaining time for the upcoming mental fatigue.

The alarm intensity setting sub-module is configured for comparing the obtained remaining time for the upcoming mental fatigue with a threshold set by a user (which can be obtained through experiments), triggering different alarm intensities, and issuing alarms according to different alarm intensities.

The alarm intensity that can be set in this system includes alarm intensity level 1, alarm intensity level 2, alarm intensity level 3, . . . ; different levels of alarm intensity correspond to different alarm sounds, voices and vibration intensities. As a preferred embodiment, the alarm intensity information is shown in Table 1.

TABLE 1

Examples of alarm intensity classification

| alarm intensity | classification basis Predicted time remaining until mental fatigue manifests | alarm sound | voice | vibration |
|---|---|---|---|---|
| Level 1 | nearly 60 minutes | low-frequency beep once | soothing tone (speech speed 1), volume 1 | none |
| Level 2 | nearly 50 minutes | low-frequency beeps twice | soothing tone (speech speed 1), volume 1 | none |
| Level 3 | nearly 40 minutes | low-frequency beeps 3 times | accelerated speech speed (speech speed 2), volume 2 | none |
| Level 4 | nearly 30 minutes | medium frequency beeps 3 times | accelerated speech speed (speech speed 2), volume 3 | none |
| Level 5 | nearly 20 minutes | medium frequency beeps 3 times | accelerated speech speed (speech speed 2), volume 4 | vibration intensity 1 |
| Level 6 | nearly 10 minutes | medium frequency beeps 3 times | accelerated speech speed (speech speed 3), volume 4 | vibration intensity 2 |
| Level 7 | nearly 5 minutes | medium frequency beeps 3 times | accelerated speech speed (speech speed 3), volume 5 | vibration intensity 3 |
| Level 8 | nearly 3 minutes | high frequency beeps 3 times | accelerated speech speed (speech speed 3), volume 6 | vibration intensity 4 |
| Level 9 | nearly 1 minute | high frequency beeps 3 times | accelerated speech speed (speech speed 4), volume 6 | vibration intensity 5 |
| Level 10 | less than 30 seconds | high frequency beeps 3 times | accelerated speech speed (speech speed 4), volume 6 | vibration intensity 6 |

2. Construction Method of Advanced Prediction Model

The advanced mental fatigue early warning system proposed by the present disclosure is implemented based on the advanced prediction model. Constructing the advanced prediction model includes the following steps:

Step 1: obtaining the pupil diameter data of the driver to be monitored, and preprocessing the obtained pupil diameter data, removing abnormal values, and performing a linear interpolation for the vacancies after removing the abnormal values, thereby obtaining the preprocessed pupil diameter data;

Step 2: defining an adjustment ability index, taking a time window for the preprocessed pupil diameter data, and obtaining the corresponding pupil diameter time series data, calculating the pupil diameter time series data within the time window to obtain the adjustment ability index time series, performing a linear prediction model modeling based on this time series; it specifically includes:

(1) Define the adjustment ability index based on pupil diameter time series

First, record the pupil diameter time series as $x^{(1)}(i)$, $1 \leq i \leq N$, where N is a length of the time series, and take a number m of points to form a vector $u_m(j)$:

$$u_m(j) = [x^{(1)}(j+k) : 0 \leq k \leq m-1]$$

where the j variable is a serial number of the points selected in order from front to back in the time series; the k variable is an offset, ranging from 0 to m−1; m is a dimension of the embedding vector $u_m(j)$, that is, the number of elements in the vector;

Second, define a distance between the two vectors $u_m(i)$ and $u_m(j)$ as d, $$d = \max_{k=0,1,\cdots,m-1} |x^{(1)}(i+k) - x^{(1)}(j+k)|$$

Then, calculate a standard deviation of the pupil diameter time series $x^{(1)}(i)$ as r, count the number of all sets of vectors $u_m(i)$ and $u_m(j)$ that satisfy d<r (add 1 if a pair of vectors meet the above condition), record it as $A_m$, and calculate $S^{(1)}$ based on $A_m$:

$$S^{(1)} = -\ln\left[\frac{A_{m+1}/(N-m-1)}{A_m/(N-m)}\right] \quad \text{(Formula 1)}$$

Then, average every 2 values of the pupil diameter time series $x^{(1)}(i)$ and use the obtained average value as a new value to form new pupil diameter time series $x^{(2)}(i)$ repeat the above steps to get $S^{(2)}$ according to Formula 1, and so on, get $S^{(3)}, S^{(4)}, \ldots, S^{(\tau)}$, where $\tau$ is a number between 10-30, this value depends on the sampling rate of the pupil diameter. The higher the sampling rate, the greater the $\tau$ value. Preferably, if the sampling rate is 100 Hz, $\tau$ is set to 10.

Finally, define the adjustment ability index as:

$$S = \frac{\sum_{i=1}^{\tau} S^{(i)}}{\tau} \quad \text{(Formula 2)}$$

(2) Calculate the adjustment ability index through sliding window

The present disclosure uses a sliding window to calculate S, and the width of the sliding window is determined by the following formula:

$$W = \frac{250\tau}{F_s} \text{(Units: s)} \quad \text{(Formula 3)}$$

where $F_S$ is the sampling frequency of pupil diameter;

The step size of the sliding window movement is between 0.1-10 s. The shorter the step size, the more conducive it is to subsequent prediction modeling (improving prediction precise), but the larger the amount of calculation is, so the step size of the present disclosure is set to 1 s.

Through calculation, the adjustment ability index time series S(n) can be obtained.

(3) Construct a prediction linear model of physiological mental fatigue adjustment ability based on the continuous values of the adjustment ability index, to obtain fatigue-related parameters, it specifically includes:

First, define a loss function:

$$\ell_{(\hat{S}-S)} = (\hat{S}-S)^2 \quad \text{(Formula 4)};$$

Second, for each input time point $t_n$, a predicted estimated value is:

$$\hat{S}_n = pt_n + b \quad \text{(Formula 5)};$$

Use the loss function to calculate a difference between the predicted estimate value and the true value:

$$\ell(\hat{S}_n-S_n)=(pt_n+b-S_n)^2$$

Then, define the average loss function as:

$$L(p, b) = \frac{1}{N2}\sum_{n=1}^{N2}\ell(\hat{S}_n - S_n)^2 = \frac{1}{N2}\sum_{n=1}^{N2}(pt_n + b - S_n)^2 \quad \text{(Formula 6)}$$

And solve the parameters (p, b) that minimize L(p, b) through Formula 7:

$$p^*, b^* = \arg\min_{p,b} L(p, b) = \arg\min_{p,b}\sum_{n=1}^{N2}(pt_n + b - S_n)^2 \quad \text{(Formula 7)}$$

Get:

$$p^* = \frac{\frac{1}{N2}\sum_{n=1}^{N2}t_n S_n - \left(\frac{1}{N2}\sum_{n=1}^{N2}t_n\right)\left(\frac{1}{N2}\sum_{n=1}^{N2}S_n\right)}{\frac{1}{N2}\sum_{n=1}^{N2}t_n^2 - \left(\frac{1}{N2}\sum_{n=1}^{N2}t_n\right)^2} \quad \text{(Formula 8)}$$

$$b^* = \bar{S} - \bar{t}p^*. \quad \text{(Formula 9)}$$

where p*, b* are the slope and intercept of the prediction linear model of physiological mental fatigue adjustment ability respectively;

(4) The mental fatigue precise prediction model is used to predict in case where a manifestation occurrence time of mental fatigue is less than or equal to 5 minutes from the current time. The construction steps include: recording for a period of time during a real-time recording process; and after obtaining time-adjustment ability index time series $(t_1,S_1), (t_2,S_2), \cdots (t_{N2},S_{N2})$ according to the above steps, establishing an autoregressive model. The order of the autoregressive model can be selected as 50, the data window is 100 s, and it is updated every 1 s to predict a waveform of 25 s.

In summary, the linear models described in Formula 5, Formula 8 and Formula 9 and the AR model described in (4) are the advanced prediction models constructed by the present disclosure. The former is used for advanced prediction, and the latter is used as more precise prediction when approaching mental fatigue. The principle is to take into account both the local periodicity and the long-term attenuation trend of the adjustment ability curve. Physiological mental fatigue increases approximately linearly with work tasks. At this time, the advanced prediction model constructed by the present disclosure uses a negative slope and a starting value at the beginning of the task as linear prediction parameters.

Figure 2:
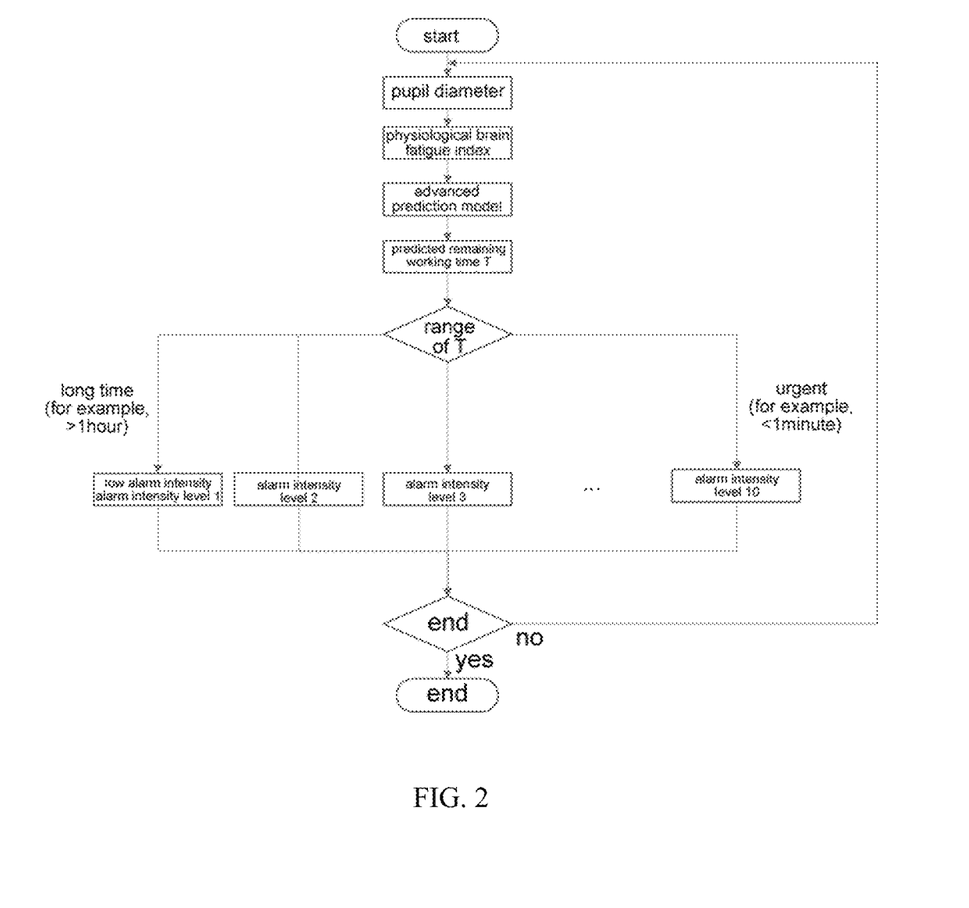
FIG. 2 is a flow chart of alarming through an advanced prediction model according to this system.

Step 3: Predict mental fatigue based on the established advanced prediction model and preset thresholds;

Based on the obtained linear prediction parameters, 3-5 (or more) thresholds can then be determined through experiments, for example, early alarm threshold (20 minutes in advance), mid-term alarm threshold (5 minutes), late alarm threshold (1 minute) and critical alarm threshold (20 seconds);

As shown in FIG. 2, this system issues alarms based on different final alarm thresholds according to the above method.

EMBODIMENTS

In order to verify the effectiveness of the system proposed in the present disclosure, its functions are verified.

1. Test System Description

Figure 3:
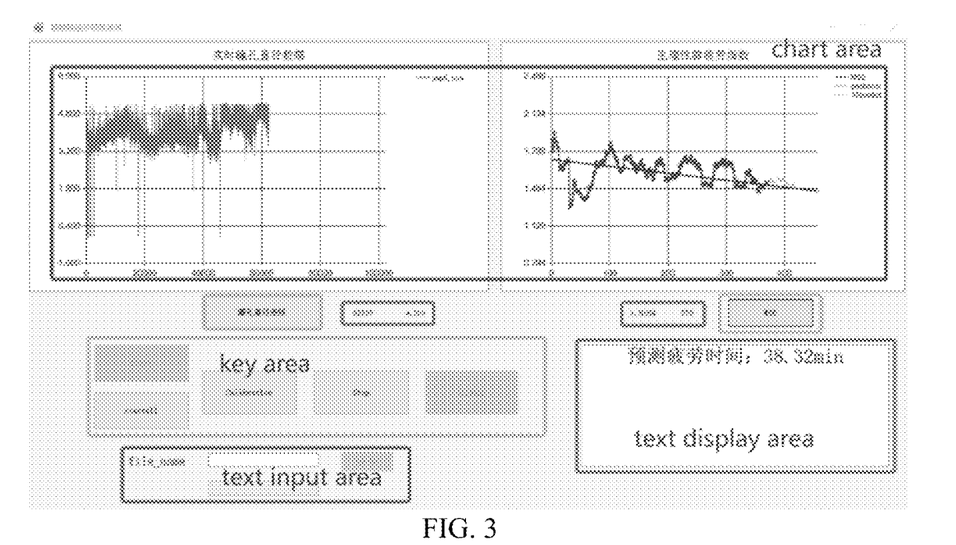
FIG. 3 shows a test interface of the mental fatigue early warning system.

In order to facilitate testing, the present disclosure designs a test interface for the mental fatigue early warning system, which is shown in FIG. 3. As can be seen from FIG. 3, it is divided into chart area, text display area, key area, and text input area.

The area framed in red is a chart area. The main function of the left half is to draw a real-time pupil diameter image that is, the data obtained from an eye tracker and the image of its relationship with time; the main function of the right half is to draw a physiological mental fatigue index image, that is, to calculate the physiological mental fatigue index by analyzing the pupil diameter data. The curve is drawn in red, and the remaining working time of the person to be monitored is predicted. Two prediction methods are used: linear model and AR model. The first drawing will start 5 minutes after the calculation starts, and its predicted images are drawn in blue and orange respectively.

The orange area is the key area or button area. The start button is configured for starting the eye tracker. Then, the eye tracker will receive the experimental data of the person to be monitored; the startall button is configured for starting drawing the pupil diameter curve and MSE curve at the same time, it is equivalent to pressing the pupil diameter curve button and the MSE button at the same time; the functions of the pupil diameter curve button and the MSE button are for starting drawing the pupil diameter curve and the MSE curve respectively; the Calibration button is configured for starting the eye tracker calibration; the stop button is configured for pausing the program; the main function of the clear button is to clear the data and reset.

The green area is the text input area, its main function is to save this data and images, and you need to enter a file name.

Figure 4:
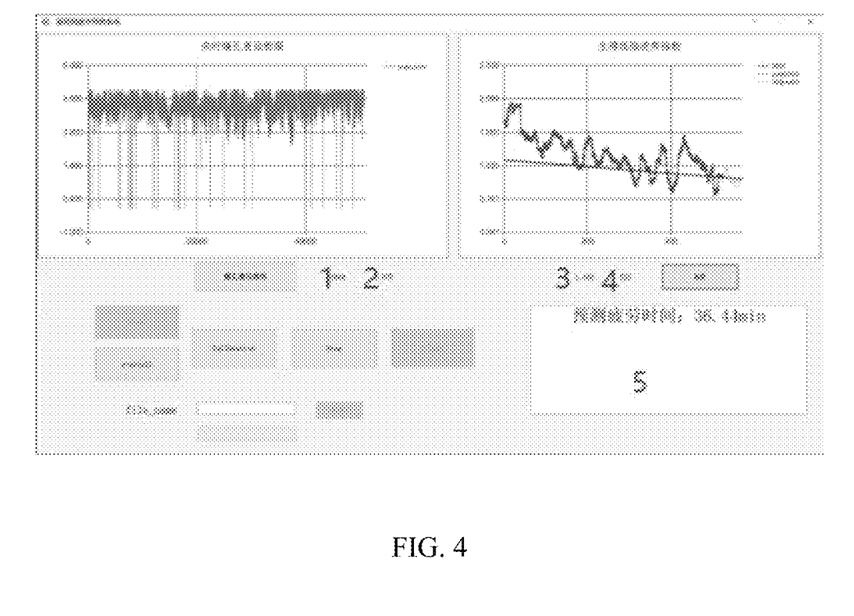
FIG. 4 shows a sub-area division of a text display area.

The blue area is the text display area, which is divided into 5 areas, as shown in FIG. 4. The value displayed in area 1 is the number of pupil data, the value displayed in area 2 is the size of the pupil, the value displayed in area 3 is the recorded size of the fatigue index, the value displayed in area 4 is the sequence number of the fatigue index point, and the value displayed in area 5 is the remaining working time of the person to be monitored. The first prediction starts 5 minutes after the calculation starts and the prediction is updated every 30 seconds.

2. Test Process

S1: Align the human eyeball with the eye tracker at a certain distance, and perform calibration according to the eye tracker calibration software process to ensure that the experimental data collected is true and reliable;

S2: Use simulation driving software to simulate driving;

S3: Enter the test interface of the mental fatigue early warning system, click the start button to start the eye tracker, then click the startall button or press the pupil diameter curve button and the MSE button in sequence. At this time, according to the user's needs, he can click the stop button to terminate the code, and he can click the clear button to clear the data or save the data through the text input area as needed, after the stop button is clicked;

S4: Preset alarm threshold time, for example, 20 minutes. When the predicted time of the mental fatigue intelligent early warning system is less than 20 minutes, a voice reminder will be issued according to the reminder method of the corresponding alarm intensity, and at the same time, observe whether the change in the predicted fatigue time increases.

3. Test Results

After executing the above test process, it can be seen from the area for the remaining working time of the person to be monitored on the test interface of the mental fatigue early warning system that, after the alarm intervention of this early warning system, the predicted fatigue time of the person to be monitored increases, and the curve also increases to a certain extent. This means that the early warning system of the present disclosure can intelligently intervene on the driver.

The basic principles, main features and advantages of the present disclosure have been shown and described above. Those skilled in the art should understand that the present disclosure is not limited by the above embodiments. The above embodiments and descriptions only illustrate the principles of the present disclosure. Various changes and modifications can be made to the present disclosure without departing from the spirit and scope of the present disclosure, those changes and modifications fall within the scope of the claimed invention. The scope of protection of the present disclosure is defined by the appended claims and their equivalents.

What is claimed is:

1. An advanced mental fatigue early warning system, comprising a data acquisition module, a preprocessing module, an adjustment ability calculation module, a fatigue early warning module, a communication module and a storage module;

the data acquisition module is configured for obtaining pupil diameter data of an operator to be monitored;

the preprocessing module is configured for preprocessing the pupil diameter data, removing invalid data, and performing linear interpolation to obtain preprocessed pupil diameter data;

the adjustment ability calculation module is configured for performing calculation based on the preprocessed pupil diameter data and correcting the preprocessed pupil diameter data through an ambient light index to obtain a constantly updated adjustment ability time series;

the fatigue early warning module is configured for performing mathematical modeling based on the obtained adjustment ability time series, establishing an advanced prediction model, and calculating a remaining time for an upcoming mental fatigue occurs and issuing an alarm;

the communication module is configured for uploading mental fatigue adjustment abilities and alarm methods to a remote server to facilitate management monitoring;

the storage module is configured for archiving intermediate data.

2. The advanced mental fatigue early warning system according to claim 1, wherein the fatigue early warning module comprises a mental fatigue occurrence time prediction sub-module and an alarm intensity setting sub-module;

the mental fatigue occurrence time prediction sub-module is configured for establishing the advanced prediction model based on the obtained adjustment ability time series, and obtaining a prediction line which has not yet occurred by means of the advanced prediction model, and then intersecting the obtained prediction line with a predetermined threshold line to calculate the remaining time for the upcoming mental fatigue;

the alarm intensity setting sub-module is configured for comparing the obtained remaining time for the upcoming mental fatigue with a threshold set by a user, triggering different alarm intensities, and issuing alarms according to different alarm intensities.

3. The advanced mental fatigue early warning system according to claim 1, wherein the alarm intensities are divided into several levels, and different levels of alarm intensity correspond to different alarm sounds, voices and vibration intensities.

4. The advanced mental fatigue early warning system according to claim 1, wherein a method for constructing the advanced prediction model comprises:

step 1: obtaining the pupil diameter data of a current person to be monitored and ambient light data, preprocessing the pupil diameter data, removing abnormal values, and performing a linear interpolation for the vacancies after removing the abnormal values, to obtain the preprocessed pupil diameter data;

step 2: defining an adjustment ability index based on the preprocessed pupil diameter data, and calculating the adjustment ability index to obtain adjustment ability index time series;

step 3: calculate the ambient light index based on the ambient light data, using an adaptive filter to remove ambient light interference, and obtaining corrected adjustment ability index time series;

step 4: constructing a mental fatigue adjustment ability prediction model based on the corrected adjustment ability index time series.

5. The advanced mental fatigue early warning system according to claim 4, wherein the step 2 comprises:

step 21: recording pupil diameter time series as $x^{(1)}(i)$, $1 \leq i \leq N$, where N is a length of the time series, and taking a number m of points to form a vector $u_m(j)$:

$$u_m(j) = [x^{(1)}(j+k) : 0 \leq k \leq m-1];$$

step 22: defining a distance between vectors $u_m(i)$ and $u_m(j)$ as d:

$$d = \max_{k=0,1,\cdots,m-1} |x^{(1)}(i+k) - x^{(1)}(j+k)|;$$

step 23: calculating a standard deviation of the time series $x^{(1)}(i)$ as r, counting the number of all sets of vectors $u_m(i)$ and $u_m(j)$ that satisfy d<r, and recording it as $A_m$;

step 24: calculating $S^{(1)}$:

$$S^{(1)} = -\ln\left[\frac{A_{m+1}/(N-m-1)}{A_m/(N-m)}\right] \qquad \text{(Formula 1)}$$

step 25: averaging every 2 values of the pupil diameter time series $x^{(1)}(i)$ as a new value to form a new time series $x^{(2)}(i)$, and repeating the steps 21-24 to get $S^{(2)}$;

step 26: repeating the step 25 to obtain $S^{(3)}, S^{(4)}, \ldots, S^{(\tau)}$ in sequence, where τ is a number in an interval [10, 30];

step 27: defining a calculation formula of the adjustment ability index as:

$$S = \frac{\sum_{i=1}^{\tau} S^{(i)}}{\tau}; \qquad \text{(Formula 2)}$$

step 28: using a sliding window to calculate S, and a setting formula for a sliding window width is:

$$W = \frac{250\tau}{F_s} \quad \text{(Formula 3)}$$

where $F_S$ is a sampling frequency of pupil diameter;

step 29: obtaining the adjustment ability index time series S(n) according to the calculated adjustment ability index.

6. The advanced mental fatigue early warning system according to claim 5, wherein the step 3 comprises:
   step 31: collecting ambient light time series y (i), $1 \leq i \leq N$ through an environmental sensor, where N is a length of the time series, and taking a number m of points to form a vector $u_m(j)$:

$u_m(j) = [y(j+k): 0 \leq k \leq m-1]$;

step 32: defining a distance between vectors $u_m(i)$ and $u_m(j)$ as d:

$$d = \max_{k=0,1,\cdots,m-1} |y(i+k) - y(j+k)|;$$

step 33: calculating a standard deviation of the time series y(i) as r, counting the number of all sets of vectors $u_m(i)$ and $u_m(j)$ that satisfy d<r, and recording it as $A_m$;
   step 34: obtaining T according to the Formula 1;
   step 35: using a sliding window to calculate T and obtaining ambient light index time series $T_1$, $T_2$, $T_3$, • • • ;
   step 36: redefining sliding window series of the adjustment ability index S(n) obtained in the step 29 as d (n), n=1, 2, • • • ;
   step 37: representing d(n) as:

$d(n) = S(n) + T_1(n), n=1, 2, \cdots$ where $T_1(n)$ is a pupil adjustment index component caused by the ambient light, $S_{(n)}$ is a real adjustment ability index component caused by a pupil;

$e(n) = d(n) - z(n), n=1, 2, \cdots$ where e(n) is an error between d(n) and an adaptive filter output z(n);
   step 38: calculating a weight vector w of the adaptive filter through an iterative method:

$w(n+1) = w(n) + \mu[p - Rw(n)]$ where n represents the number of iterations, μ represents a positive constant, p is a cross-correlation vector of the data, and R is a correlation matrix of the data;
   step 39: obtaining the corrected adjustment ability index time series based on the obtained e(n).

7. The advanced mental fatigue early warning system according to claim 5, wherein the constructed prediction model comprises a mental fatigue advanced prediction model configured to work in case where a manifestation occurrence time of mental fatigue is greater than 5 minutes from the current time and a mental fatigue precise prediction model configured to work in case where the manifestation occurrence time of mental fatigue is less than or equal to 5 minutes from the current time, approaching threshold:
   (1) the mental fatigue advanced prediction model is constructed in the following steps:
   step 41: define a loss function of the adjustment ability index time series:

$\ell(\hat{S} - S) = (\hat{S} - S)^2$ \quad (Formula 4);

step 42: for each input time point $t_n$, a predicted estimated value is:

$\hat{S}_n = pt_n + b$ \quad (Formula 5)

step 43: defining an average loss function as:

$$L(p, b) = \frac{1}{N2}\sum_{n=1}^{N2}\ell(\hat{S}_n - S_n)^2 = \frac{1}{N2}\sum_{n=1}^{N2}(pt_n + b - S_n)^2; \quad \text{(Formula 6)}$$

step 44: solving parameters which minimize L(p, b) according to Formula 7:

$$p^*, b^* = \arg\min_{p,b} L(p, b) = \arg\min_{p,b}\sum_{n=1}^{N2}(pt_n + b - S_n)^2; \quad \text{(Formula 7)}$$

and:

$$p^* = \frac{\frac{1}{N2}\sum_{n=1}^{N2} t_n S_n - \left(\frac{1}{N2}\sum_{n=1}^{N2} t_n\right)\left(\frac{1}{N2}\sum_{n=1}^{N2} S_n\right)}{\frac{1}{N2}\sum_{n=1}^{N2} t_n^2 - \left(\frac{1}{N2}\sum_{n=1}^{N2} t_n\right)^2} \quad \text{(Formula 8)}$$

$b^* = \bar{S} - \bar{t} p^*$ \quad (Formula 9)

(2) the mental fatigue precise prediction model is constructed in the following steps:
   step 45: recording for a period of time during a real-time recording process;
   step 46: after obtaining time-adjustment ability index time series $(t_1, S_1)$, $(t_2, S_2)$, • • • $(t_{N2}, S_{N2})$ according to the above steps, establishing an autoregressive model,
   step 47: an order of the autoregressive model is selected as 50, a data window is 100 s, and it is updated every is to predict a waveform of 25 s.

8. An electronic device, comprising:
   at least one processor; and
   a memory communicatively connected to the at least one processor;
   wherein the memory is configured to store instructions executable by the at least one processor, the instructions are executed by the at least one processor, so that the at least one processor executes the steps in claim 4.

9. A computer-readable storage medium storing computer instructions, wherein the computer instructions are used to allow a computer to execute the steps in claim 4.

* * * * *